United States Patent [19]

Asselin et al.

[11] Patent Number: 4,925,955

[45] Date of Patent: May 15, 1990

[54] RESOLUTION OF (1S,4R)-1-ETHYL-1,3,4,9-TETRAHYDRO-4-(PHENYLMETHYL) PYRANO[3,4-B]INDOLE-1-ACETIC ACID USING BRUCINE

[75] Inventors: Andre A. Asselin, Lawrenceville, N.J.; Jean Schmid, Yardley, Pa.

[73] Assignee: American Home Products Corporation, New York, N.Y.

[21] Appl. No.: 316,623

[22] Filed: Feb. 28, 1989

[51] Int. Cl.$^5$ ............................................. C07D 493/04
[52] U.S. Cl. ................................................... 548/432
[58] Field of Search ........................................ 548/432

[56] References Cited

U.S. PATENT DOCUMENTS

| | | | |
|---|---|---|---|
| 4,501,899 | 2/1985 | Abraham et al. | 548/432 |
| 4,520,203 | 5/1985 | Abraham et al. | 548/432 |
| 4,604,469 | 8/1986 | Demerson et al. | 548/432 |
| 4,670,462 | 6/1987 | Katz et al. | 514/411 |

OTHER PUBLICATIONS

Jean Jacques, André Collet, and Samuel H. Wilen, *Enantiomers, Racemates, and Resolutions,* 1981, pp. 256–259, 384, 385.

William Henry Perkin, William Jackson Pope, and Otto Wallach, Optically Active Substances Containing No Asymetric Atom, 1-Methylcyclohexylidene-4-Acetic Acid, *Journal of The Chemical Society,* 1909, vol. 95, pp. 1789–1802.

A. Katz et al., J. Med. Chem., 31, 1244–1250, (1988).

*Primary Examiner*—Anton H. Sutto
*Assistant Examiner*—Edward Rosfjord
*Attorney, Agent, or Firm*—Walter Patton

[57] ABSTRACT

This invention relates to a process for resolving (±)-cis-1-ethyl-1,3,4,9-tetrahydro-4-(phenylmethyl)pyrano[3,4-b]indole-1-acetic acid (pemedolac) usinig brucine to obtain the corresponding (1S,4R)-eutomer. Said eutomer is useful as an analgesic.

1 Claim, No Drawings

RESOLUTION OF (1S,4R)-1-ETHYL-1,3,4,9-TETRAHYDRO-4-(PHENYLMETHYL) PYRANO[3,4-B]INDOLE-1-ACETIC ACID USING BRUCINE

BACKGROUND OF THE INVENTION

This invention relates to a process for resolving (±)-cis-1-ethyl-1,3,4,9-tetrahydro-4-(phenylmethyl)-pyrano[3,4-b]indole-1-acetic acid using brucine and preferential crystallization of the enriched free acid to obtain the corresponding (1S,4R)-enantiomer.

(±)-cis-1-Ethyl-1,3,4,9-tetrahydro-4-(phenylmethyl)-pyrano[3,4-b]indole-1-acetic acid, an optically inactive racemic mixture, is known generically as pemedolac, and as an analgesic agent described in Katz et al U.S. Pat. No. 4,670,462.

Pemedolac possesses the 4-(phenylmethyl) group and the 1-acetic acid on the same side of a plane containing the flat indole nucleus. The molecule is asymetric and is obtained as a mixture of two optical isomers. A. H. Katz, C. A. Demerson, et al., J. Med. Chem., 31, 1244–1250 (1988) describes the resolution of (±)-pemedolac via the chromatographic separation of its diastereomeric esters with [(1S)-endo]-(−)-borneol, followed by hydrolysis. Pemedolac is a potent analgesic agent and the analgesic effect was found to reside in (+)-pemedolac, the (1S,4R)-enantiomer. The absolute configuration was assigned on the basis of a crystallographic analysis of the (S)-(−)-borneol ester.

The present process avoids the tedious and expensive chromatographic separation previously reported, and provides the eutomer, the (1S,4R)-enantiomer, in high yield and in a commercially feasible operation.

SUMMARY OF THE INVENTION

The process for preparing (1S,4R)-1-ethyl-1,3,4,9-tetrahydro-4-(phenylmethyl)pyrano[3,4-b]indole-1-acetic acid comprises:

(1) mixing one part by weight of (±)-pemedolac and 1.0 to 1.3 parts by weight of brucine, (2) crystallizing out the distomer, the (1R,4S)-enantiomer, with brucine, (3) concentrating the mother liquors; then taking the residual enriched enantiomeric mixture of eutomer with brucine back in a mixture of a water-immiscible organic solvent and an aqueous mineral acid; separating the organic layer; and isolating an enriched enantiomeric mixture of eutomer as free acid, (4) crystallizing the later enriched enantiomeric mixture of eutomer to directly afford high yields of enantiomerically pure (1S,4R)-1-ethyl-1,3,4,9-tetrahydro-4-(phenylmethyl)pyrano[3,4-b]indole-1-acetic acid.

DETAILED DESCRIPTION OF THE INVENTION

The present invention discloses the resolution of (±)-pemedolac by a method (Scheme I)

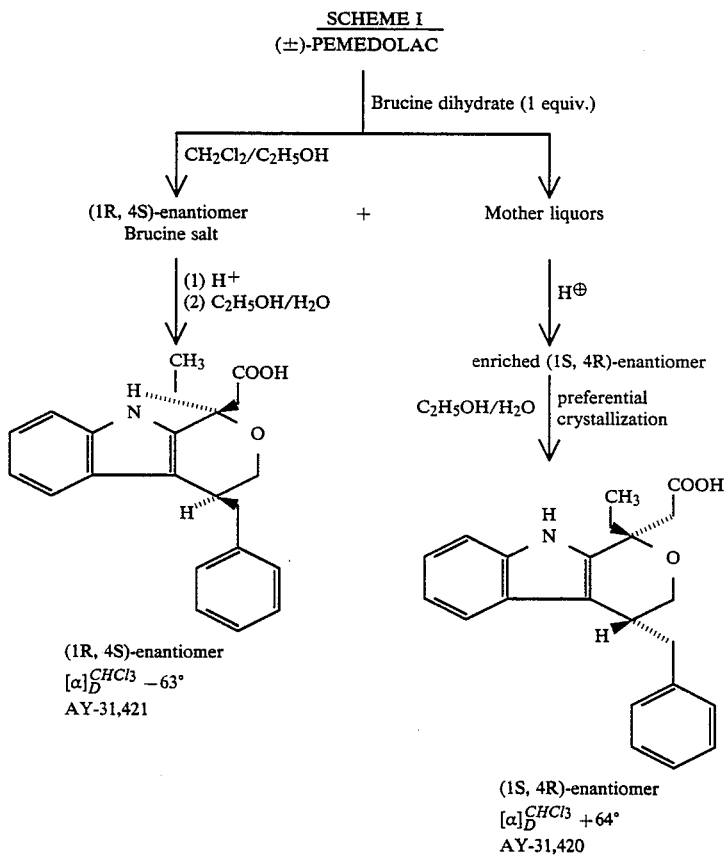

which avoids the use of chromatographic procedures and provides each enantiomer in good yield and high enantiomer purity. In contrast with the previously published procedure, the present method allows the preparation of large quantities of the two enantiomers. The separation of the optical isomers was done via fractional crystallization of the diastereomeric salts of (±)-pemedolac with brucine. Molar equivalents of (±)-pemedolac and brucine dihydrate were dissolved in hot ethanol. Upon standing at room temperature for four hours, a thick suspension of crystals formed. This solid was collected by filtration, and the filtrate was set aside. The solid salt was recrystallized once from methylene chloride and ethanol. Regeneration of the free acid with aqueous hydrochloric acid gave the inactive (1R,4S)-enantiomer of pemedolac. Crystallization from ethanol and water afforded a white crystalline compound. HPLC analysis on a Cyclobond Beta column (25 cm, solvent system: 24% acetonitrile/76% 0.01M ammonium phosphate pH 3.5, flow rate: 1.4 ml/min., detector UV at 210 mm) revealed an enantiomeric purity of better than 99.5%. This material had a melting point of 170°–171° C. and an optical rotation of −62.97° (CHCl$_3$).

The filtrate from the first brucine salt crystallization was evaporated, and the residue was partitioned between aqueous hydrochloric acid and ether. The organic layer was washed several times with acid to remove any trace of brucine and concentrated down to a white foam. HPLC analysis using the conditions described above indicated that the material contained a 4:1 ratio of the optical isomers in favor of the active (1S,4R)-enantiomer.

A crystalline brucine salt of this enantiomer, or any other diastereomeric salts with resolving bases could not be crystallized preferentially. However, it was found that this enriched mixture could be crystallized as the free acid to afford the (1S,4R)-enantiomer leaving the (1R,4S)-enantiomer in the mother liquor. Two crystallizations from ethanol and water afforded 99.9% enantiomerically pure product as determined by HPLC analysis. This material had a melting point of 170°–171° C. and an optical rotation +64.28° (CHCl$_3$).

Using this method, both enantiomers could be efficiently prepared in more than 60% of the theoretical yield.

The following examples further illustrate this invention.

EXAMPLE 1

Preparation of (1R,4S)-(−)-1-Ethyl-1,3,4,9-tetrahydro-4-(phenylmethyl)pyrano[3,4-b]indole-1-acetic Acid (±)-cis-1-Ethyl-4-(phenylmethyl)-1,3,4,9-tetrahydropyrano[3,4-b]indole-1-acetic acid (isomer A, prepared by the process of Katz et al, U.S. Pat. No. 4,670,462, Example 1, 100 g, 0.29 mol) and brucine dihydrate (123 g, 0.29 mol) were dissolved together in hot ethanol (1.2 L). The solution was filtered through a fluted filter paper and left to stand at room temperature for 4 hours. The (1R, 4S)-pemedolac brucine salt crystallized out to form a thick suspension. The solid was collected by filtration and washed with ethanol (200 mL) to give a white compound (97 g, m.p. 138°–140° C.). (The filtrate was set aside and processed as in Example 2 herein below to obtain the (1S,4R)-enantiomer.) The solid was recrystallized from methylenechloride (1 L) and ethanol (1.5 L). The clear solution was evaporated on a rotovap until the compound started to crystallize out and the total volume was brought down to approximately half a liter. After standing in the refrigerator overnight the solids were collected and washed with ethanol (100 mL) to give a white compound (89.7 g, m.p. 138°–140° C.). Analytical LC on Cyclobond column (solvent system: 24% acetonitrile/76% 0.01M ammonium phosphate, pH 3.5) indicated more than 99% isomeric purity.

The (1R,4S)-pemedolac brucine salt (88 g) was suspended in ether (700 mL). To this was added with stirring 1N hydrochloric acid (500 mL). The organic layer was separated and washed with 1N hydrochloric acid and water. It was dried over magnesium sulfate, filtered and evaporated to give a white foam (38.5 g). Crystallization from ethanol (250 mL) and water (100 mL) afforded a white crystalline compound (32.8 g, 65%, m.p. 170°–171° C.). The material was air-dried, then pulverized and dried in high vacuum at 78° C. for 63 hours. Analytical LC showed 99.7% enantiomeric purity and the optical rotation in chloroform at room temperature was −63°. NMR indicated that 4 mole % ethanol (0.5 weight %) was present in the dried product.

Anal. Calc'd for $C_{22}H_{23}NO_3$: C, 75.62; H, 6.63; N, 4.01% Found C, 75.89; H, 6.65; N, 3.88%.

EXAMPLE 2

Preparation of (1S,4R)-(+)-1-Ethyl-1,3,4,9-tetrahydro-4-(phenylmethyl)pyrano[3,4-b]indole-1-acetic Acid The filtrate of the (1R,4S)-pemedolac brucine salt (obtained in Example 1) was concentrated down to an oil. Analytical LC on Cyclobond column (solvent system: 24% acetonitrile/76% 0.01M ammonium phosphate, pH 3.5) indicated 80% isomeric purity in favor of the (1S,4R)-isomer. The material was partitioned between 1N HCl and ether. The organic layer was separated and washed five times with 1N hydrochloric acid to remove any traces of brucine. It was then washed with water, dried over magnesium sulfate, filtered and evaporated to give a white foam (56.6 g). Crystallization from warm ethanol (300 mL) and water (100 mL) afforded a white compound (34 g, yield: 68%). Analytical LC showed 97% enantiomeric purity. One more recrystallization from warm ethanol (150 mL) and water (100 mL) under stirring for 0.5 hours at room temperature and at 0° C. for 1 hour afforded 99.9% enantiomerically pure product as a white powder (30.0 g, m.p. 170°–171° C., yield: 60%). The material was air-dried, pulverized, and dried in high vacuum at 78° C. for 63 hours. The optical rotation in chloroform at room temperature was +64°. NMR indicated that 4 mole % ethanol (0.5 weight %) was present in the dried product.

Anal. Calc'd for $C_{22}H_{23}NO_3$: C, 75.62; H, 6.63; N, 4.01% Found C, 75.86; H, 6.65; N, 3.90%.

We claim:

1. An improved process for preparing (1S,4R)-(+)-1-ethyl-1,3,4,9-tetrahydro-4-(phenylmethyl)pyrano[3,4-b]indole-1-acetic acid which comprises
   (a) dissolving one part by weight of (±)-1-ethyl-4-(phenylmethyl)-1,3,4,9-tetrahydro[3,4-b]indole-1-acetic acid and about 1.0 to 1.3 parts by weight of brucine in a minimal amount of hot ethanol;
   (b) cooling the solution to crystallize the brucine salt of the distomer (1R,4S)-(−)-1-ethyl-1,3,4,9-tetrahydro-4-(phenylmethyl)pyrano[3,4-b]indole-1-acetic acid;
   (c) removing said brucine salt of the distomer by filtration; wherein the improvement comprises
   (d) concentrating the mother liquors;
   (e) dissolving the brucine salt of the enriched eutomer in a mixture of ether and dilute aqueous hydrochloric acid;
   (f) separating the ether layer; and
   (g) isolating substantially pure (1S,4R)-(+)-1-ethyl-1,3,4,9-tetrahydro-4-(phenylmethyl)pyrano[3,4-b]indole-1-acetic acid by preferrential crystallization from ethanol water.

* * * * *